(12) United States Patent  (10) Patent No.: US 7,789,823 B2
Kato et al.  (45) Date of Patent: Sep. 7, 2010

(54) ENDOSCOPE AND ENDOSCOPE APPARATUS

(75) Inventors: Takayuki Kato, Hachioji (JP); Kazuhiro Kumei, Tachikawa (JP)

(73) Assignee: Olympus Corporation, Tokyo (JP)

( * ) Notice: Subject to any disclaimer, the term of this patent is extended or adjusted under 35 U.S.C. 154(b) by 972 days.

(21) Appl. No.: 11/595,278

(22) Filed: Nov. 9, 2006

(65) Prior Publication Data
US 2007/0055100 A1  Mar. 8, 2007

Related U.S. Application Data

(63) Continuation of application No. PCT/JP2005/008483, filed on May 10, 2005.

(30) Foreign Application Priority Data
May 14, 2004  (JP) .............................. 2004-145578

(51) Int. Cl.
*A61B 1/04* (2006.01)
(52) U.S. Cl. ................ 600/109; 600/176; 348/340
(58) Field of Classification Search ............. 600/104, 600/109, 176, 167, 168; 348/340, 65, 68, 348/69
See application file for complete search history.

(56) References Cited

U.S. PATENT DOCUMENTS

| | | | | |
|---|---|---|---|---|
| 5,436,767 A | * | 7/1995 | Suzuki et al. | ............. 359/716 |
| 5,463,496 A | * | 10/1995 | Ise | ............. 359/497 |
| 5,828,498 A | * | 10/1998 | Sekiya et al. | ............. 359/660 |
| 6,025,873 A | | 2/2000 | Nishioka et al. | |
| 6,066,090 A | | 5/2000 | Yoon | |
| 6,241,656 B1 | * | 6/2001 | Suga | ............. 600/109 |
| 6,433,937 B1 | | 8/2002 | Konno | |
| 6,582,362 B2 | * | 6/2003 | Konno | ............. 600/167 |
| 7,537,561 B2 | * | 5/2009 | Yamaya et al. | ............. 600/106 |
| 2003/0133036 A1 | * | 7/2003 | Takada | ............. 348/362 |
| 2003/0191368 A1 | * | 10/2003 | Wang et al. | ............. 600/160 |
| 2005/0277186 A1 | * | 12/2005 | Fein et al. | ............. 435/288.7 |

FOREIGN PATENT DOCUMENTS

EP  1 211 543  6/2002

(Continued)

OTHER PUBLICATIONS

European Supplementary Search Report dated Dec. 3, 2009, issued in corresponding European Patent Application No. 05739136.9.
International Search Report, Application No. PCT/JP2005/008483 filed on May 10, 2005.

*Primary Examiner*—John P Leubecker
(74) *Attorney, Agent, or Firm*—Kenyon & Kenyon LLP

(57) ABSTRACT

This endoscope is equipped with a fixed focus image pickup unit which is constructed of an objective optical system, and a solid state color image pickup device in which a color filter is arranged every pixel, the solid state image pickup device fulfilling a conditional expression (300<IH/P<550), and the objective optical system fulfilling a conditional expression (300<Fl/P<550) and a conditional expression (2400× P<Fno.<4200×P), and an image pickup plane of the solid state image pickup device is arranged in a position where an MTF on an optical axis in a spatial frequency 1/(3×P) of the objective optical system at 4 mm of object distance, and an MTF on the optical axis in a spatial frequency 1/(3×P) at 50 mm of object distance become 10% or more together.

12 Claims, 5 Drawing Sheets

FOREIGN PATENT DOCUMENTS

| | | |
|---|---|---|
| JP | 10-216077 | 2/1998 |
| JP | 2000-267002 | 9/2000 |
| JP | 2000-330015 | 11/2000 |
| JP | 2001-033710 | 2/2001 |
| JP | 2004-350848 | 12/2004 |

* cited by examiner

ENDOSCOPE AND ENDOSCOPE APPARATUS

CROSS REFERENCE TO RELATED APPLICATION

This application is a continuation application of PCT/JP2005/008483 filed on May 10, 2005 and claims benefit of Japanese Application No. 2004-145578 filed in Japan on May 14, 2004, the entire contents of which are incorporated herein by this reference.

BACKGROUND OF THE INVENTION

1. Field of the Invention

The present invention relates to an endoscope and an endoscope apparatus, and in particular, to an electronic endoscope equipped with a fixed focus image pickup unit constructed of an objective optical system and a solid state image pickup device.

2. Description of the Related Art

In an endoscope which is equipped with a so-called fixed focus image pickup unit in which a solid state image pickup device is fixed to an image position of an objective optical system and there is no movable part, it is possible to simplify and lessen the structure of the image pickup unit, and thus it is advantageous in respect of cost reduction, lessening of an outer diameter of an endoscope insertion section, and shortening length of a rigid end section. In addition, since there is no need for focusing, a user can concentrate on the operation of an endoscope and easily treat it, and hence, it is used widely in various fields such as medical use and industrial use.

In an endoscope equipped with such a fixed focus image pickup unit, a focus position where a clear image can be obtained also in a distant view (for example, about 50 to 100 mm in the case of a common medical use endoscope) is set so as to perform an operation of guiding an endoscope insertion section end to a position which it is intended to observe, and a so-called screening that selects a desired observation position with watching a large area. In addition, it is common that, when a distance between an endoscope insertion section end and an object is shortened, an object distance in which a clear image is obtained is up to about 5 to 10 mm.

When it is required to observe an object in detail enlargingly, it is conceivable to provide and construct a so-called zoom image pickup unit which enables a zooming operation (zooming) of moving a lens in an objective optical system to change a focal length and an operation distance. As to endoscopes equipped with such a zoom image pickup unit, various proposals such as Japanese Patent Laid-Open No. 2000-330015, and Japanese Patent Laid-Open No. 2001-33710 have been made up to now.

In an endoscope equipped with a zoom image pickup unit, it is possible to obtain almost the same depth of field as that of an endoscope equipped with a fixed focus image pickup unit at a so-called wide end at which a focal length becomes short. Therefore, in this case, usage similar to that of an endoscope equipped with a fixed focus image pickup unit can be performed. In addition, since a depth of focus approaches toward a near point (becomes shallow) at a so-called tele end where a focal length becomes long in comparison with the wide end, it becomes out of focus at a distant view (about 50 to 100 mm). Instead, it is possible to obtain a clear image when a distance between an endoscope insertion section end and an object approaches (for example, from about 2 mm to 3 mm in the case of an endoscope equipped with a general zoom image pickup unit). Hence, it is possible to enlargingly observe an object in detail.

SUMMARY OF THE INVENTION

An endoscope of the present invention is an endoscope being equipped with a fixed focus image pickup unit which is constructed of an objective optical system, and a solid state color image pickup device in which a color filter is arranged every pixel, the image pickup unit is constructed of a solid state image pickup device of fulfilling the following expression:

$$300 < IH/P < 550 \qquad \text{conditional expression (1)}$$

where

P is a horizontal pixel pitch [mm] of a solid state image pickup device, and

IH: distance [mm] to most distant position from center in display area of solid state image pickup device, and an objective optical system having characteristics of fulfilling the following expressions for a pixel pitch P (mm) of the solid state image pickup device:

$$300 < Fl/P < 550 \qquad \text{conditional expression (2)}$$

where

Fl: focal length [mm] of objective optical system and $$2400 \times P < Fno. < 4200 \times P \qquad \text{conditional expression (3)}$$

where

Fno.: effective f-number of objective optical system, and is characterized in that an image pickup plane of the solid state image pickup device is arranged in a position where an MTF on an optical axis in a spatial frequency $1/(3 \times P)$ of an objective optical system at 4 mm of object distance, an MTF on the optical axis in the spatial frequency $1/(3 \times P)$ at 50 mm of object distance become 10% or more together.

In addition, an endoscope apparatus of the present invention is equipped at least an endoscope including a fixed focus image pickup unit constructed of a solid state image pickup device in which a color filter is arranged every pixel and which fulfills the above-mentioned conditional expression (1), and an objective optical system which fulfills the above-mentioned conditional expression (2), and the above-mentioned conditional expression (3), and display means which displays an image which the image pickup unit acquires, characterized in that, with letting a range of the image pickup unit in an object side, where resolution in a center of an image displayed on the display means is 25 lines/mm or more, be d1, and letting a range of the image pickup unit in an object side, where resolution in a center of an image displayed on the display means is 2 lines/mm or more, be d2, an image pickup plane of a solid state image pickup device is arranged near an image forming position of an objective optical system so that an object point on the optical axis which is at a position apart by 3.5 mm from a plane of the objective optical system in a side nearest to the object which constructs an image pickup unit may be included in both of d1 and d2, and so that an object point on the optical axis which is at a position apart by 50 mm from a plane of the objective optical system in a side nearest to the object which constructs the image pickup unit may be included in only d2.

In addition, an endoscope apparatus of the present invention is an endoscope apparatus which is equipped with a fixed focus image pickup unit which forms an objective image with an objective optical system which fulfill the above-mentioned conditional expression (2) and the above-mentioned conditional expression (3), in which a color filter is arranged every pixel near an image-formation plane of the objective optical system, and which acquires an image signal with a solid state image pickup device which fulfills the above-mentioned conditional expression (1), and a circuit system which processes the image signal sent from the solid state image pickup device, and characterized in that this endoscope apparatus has a resolution of 35 μm or more when a distance from the objective optical system to an object is 4 mm, and has a resolution of 0.45 mm or more when the distance from the objective optical system to the object is 50 mm.

In addition, an endoscope apparatus of the present invention is an endoscope equipped with a fixed focus image pickup unit which is constructed of an objective optical system, and a solid state image pickup device which generates a luminance signal every pixel, the above-mentioned image pickup unit is constructed of a solid state image pickup device of fulfilling the following expression:

$$200 < IH/P < 360 \quad \text{conditional expression (4)}$$

where

P: horizontal pixel pitch [mm] of solid state image pickup device, and

IH: distance [mm] to most distant position from center in display area of solid state image pickup device, and an objective optical system having characteristics of fulfilling the following expressions for a pixel pitch P (mm) of the solid state image pickup device:

$$200 < Fl/P < 360 \quad \text{conditional expression (5)}$$

where

Fl: focal length [mm] of objective optical system and $$1600 \times P < Fno. < 2800 \times P \quad \text{conditional expression (6)}$$

where

Fno.: effective f-number of objective optical system, and is characterized in that an image pickup plane of the solid state image pickup device is arranged in a position where an MTF on an optical axis in a spatial frequency $1/(2 \times P)$ of an objective optical system at 4 mm of object distance, an MTF on the optical axis in the spatial frequency $1/(2 \times P)$ at 50 mm of object distance become 10% or more together.

In addition, an endoscope apparatus of the present invention is an endoscope apparatus equipped at least with an endoscope at least including a fixed focus image pickup unit constructed of a solid state image pickup device in which a luminance signal is generated every pixel, and which fulfills the above-mentioned conditional expression (4), and an objective optical system which fulfills the above-mentioned conditional expression (5) and the above-mentioned conditional expression (6), and display means which displays an image which the image pickup unit acquires, the endoscope apparatus is characterized in that, with letting a range of the image pickup unit in an object side, where resolution in a center of an image displayed on the display means is 25 lines/mm or more, be d1, and letting a range of the image pickup unit in an object side, where resolution in a center of an image displayed on the display means is 2 lines/mm or more, be d2, an image pickup plane of a solid state image pickup device is arranged near an image forming position of an objective optical system so that an object point on the optical axis which is at a position apart by 3.5 mm from a plane of the objective optical system in a side nearest to the object which constructs an image pickup unit may be included in both of d1 and d2, and so that an object point on the optical axis which is at a position apart by 50 mm from a plane of the objective optical system in a side nearest to the object which constructs the image pickup unit may be included in only d2.

In addition, an endoscope apparatus of the present invention is an endoscope apparatus which is equipped with a fixed focus image pickup unit which forms an objective image with an objective optical system which fulfill the above-mentioned conditional expression (5) and the above-mentioned conditional expression (6), in which a color filter is arranged every pixel near an image-formation plane of the objective optical system, and which acquires an image signal with a solid state image pickup device which fulfills the above-mentioned conditional expression (4), and a circuit system which processes the image signal sent from the solid state image pickup device, and characterized in that the endoscope apparatus has a resolution of 35 μm or more when a distance from the objective optical system to an object is 4 mm, and has a resolution of 0.45 mm or more when the distance from the objective optical system to the object is 50 mm.

Here, a definition of a resolution will be explained.

When a point image is formed by an optical system which has an almost aplanatic circular opening, an objective image becomes an Airy disc which is a diffraction image of the circular opening. When two points with equal intensity exist close to each other, it becomes an intensity distribution as shown in FIG. 4 since these diffraction images overlap.

FIG. 4 is a graph showing the intensity distribution on a straight line passing through an intensity center of two diffraction images, and a horizontal axis represents a distance (unit: mm), and, a vertical axis expresses intensity (arbitrary unit). Rayleigh (person's name) made a gap between these two diffraction images being equal to a radius of the Airy disc a limit that two point images are identified as two. Thereafter, this has been a criterion called a Rayleigh criterion. At this time, an intensity distribution of a diffraction image becomes in a state where a valley which has 74% of intensity to a vertex is left. ("Optical Technical Handbook" published by Asakura Publishing Co., Ltd.)

Then, in the present invention, assuming that a state where a valley of a distribution intensity between two points is 74% or less to a vertex is "resolving", a distance of a limit of resolving is defined as a "resolution".

Specifically, as shown in FIG. 5, two points placed in front of an objective optical system 5 arranged at an end of an insertion section of an endoscope 4 are captured so that two point images may stand in a line in a horizontal direction on an image pickup plane of a solid state image pickup device 1 (that is, two point images stand in a line on a screen of a monitor 7 horizontally), an output signal from a circuit system 6 which processes an image signal from the solid state image pickup device 1 is caught with an oscilloscope 9, and an intensity distribution of two point images is measured. At this time, a minimum distance between two points which is "resolved" is made a "resolution".

In addition, at this time, as shown in FIG. 6, a black and white line pair may be substituted for two points put in order horizontally. When a "resolution" is used in the present invention, it points to a value obtained by the above-mentioned method.

Next, a resolution power is defined as follows.

In FIG. 6, black and white line pairs placed in front of the objective optical system 5 arranged at an end of an insertion section of the endoscope 4 are captured so that black and white stripes may align in a horizontal direction on an image pickup plane of the solid state image pickup device 1, and are displayed on the monitor 7 through the circuit system 6 which processes the image signal sent from the solid state image pickup device 1. At this time, an intensity distribution of the black and white obtained on the screen of the monitor 7 becomes as shown in FIG. 7.

FIG. 7 is a graph showing a signal wave form when catching a horizontal image signal outputted from the monitor 7 with an oscilloscope (not shown in FIG. 6), and the horizontal axis expresses a horizontal position on a monitor screen, and the vertical axis expresses signal intensity, respectively.

Here, let a maximum value of an intensity distribution shown in FIG. 7 be Imax and let a minimum value be Imin, and contrast I of black and white line pairs on the monitor are obtained as follows:

$$I=(Imax-Imin)/(Imax+Imin) \qquad (i)$$

The resolution power is defined as an inverse of a width of a black and white line pair in case the above-mentioned contrast I becomes 10%.

Hence, description of "a resolution power is 25 lines/mm or more" and "a resolution power is 2 lines/mm or more" which are described above indicates that the contrast of a black and white line pair with 40 μm or less of width and 0.5 mm or less of width is 10% or more on a monitor, respectively.

In addition, in the present invention, it is assumed that an "MTF" denotes a mean value of MTFs in respective wavelengths of the d-line (wavelength of 587.6 nm), e-line (wavelength of 546.1 nm), and f-line (wavelength of 486.1 nm).

Furthermore, here, a "display area" and the "IH" of a solid state image pickup device will be explained simply.

An endoscope apparatus is mainly constructed of the endoscope 4, circuit system 6 which processes an image signal, and the image display monitor 7, as shown in FIG. 3. An image picked up with the image pickup unit which is constructed of the objective optical system 5 and solid state image pickup device 1 is processed by the circuit system 6 which processes an image signal, and is displayed on the image display monitor 7. A "display area" of the solid state image pickup device 1 points to an area on the solid state image pickup device 1 corresponding to a range displayed on the above-mentioned image display monitor 7.

Hence, when a display range is limited with an octagonal visual field mask on the image display monitor 7, a display area 3 formed on an effective pixel area 2 of the solid state image pickup device 1 also becomes a similar form as shown in FIG. 1.

In addition, as another example, when a display range on the image display monitor 7 is limited with a circular form only in left and right directions, the display area 3 formed on the effective pixel area 2 of the solid state image pickup device 1 also becomes a similar form as shown in FIG. 2.

Furthermore, when there is no visual field mask and a full-screen display is performed on the image display monitor 7, the effectiveness pixel area 2 of the solid state image pickup device 1 corresponding to a form of a display unit of the image display monitor 7 becomes a display area.

Moreover, the IH is a distance to the most distant position from a center in the display area of the solid state image pickup device 1. Generally, this is called image height.

Next, a definition of a depth of field will be explained simply here.

In a common endoscope, the case where a solid state image pickup device with a pixel pitch P is arranged in an image surface position Xb' in the case of making a best distance be Xb will be considered. On a condition that the solid state image pickup device is fixed, when an object is approached to Xn, an image surface position Xn' at the time of approach will deviate from the image pickup plane position of a solid state image pickup device.

At this time, let a largest circle of confusion that can be regarded as focused be a permissible circle of confusion, and let its diameter be δ, and when it can be recognized that a diameter of a circle of confusion in the image pickup plane of the solid state image pickup device is smaller than δ, it is possible to regard that an object image from Xb to Xn is focused. That is, it is possible to define that a range until a diameter of a circle of confusion coincides to δ is a depth of field in a near point side.

At this time, the following expression holds from Newton's image equations:

$$(1/Xn)-(1/Xb)=\delta Fno./Fl^2 \qquad (ii)$$

Similarly, an expression of a depth of field in a far point side is defined as follows:

$$(1/Xb)-(1/Xf)=\delta Fno./Fl^2 \qquad (iii)$$

When the expressions (ii) and (iii) are united, the following expressing holds:

$$(1/Xn)-(1/Xf)=\delta Fno./Fl^2 \qquad (iv)$$

Nevertheless, it is made that a best distance is Xb, a distance up to a near point of a depth of field is Xn, a distance up to a far point of the depth of field is Xf, a diameter of a permissible circle of confusion is δ, a focal length of an optical system is Fl, and an effective f-number of the optical system is Fno.

The above-described conditional expression (1) and the conditional expression (4) specify conditions of a solid state image pickup device to be used in the present invention, and show a range within which a ratio of a pixel pitch of the solid state image pickup device to a maximum image height should be.

Generally, since the diameter δ of the permissible circle of confusion is proportional to the pixel pitch of a solid state image pickup device, δ to the image height IH becomes small as the value of IH/P is large. For this reason, when the value of IH/P becomes too large, a large depth of field is no longer obtained, and it becomes impossible to achieve the object of the present invention.

On the other hand, since the pixel pitch of the solid state image pickup device to the image height IH becomes large although the depth of field becomes large when the value of IH/P becomes small, a sampling interval of the solid state image pickup device becomes long. Hence, a resolution to an image with a fixed magnification drops. When the value of IH/P becomes too small, a required resolution is not obtained even at a most near point in the depth of field, or it becomes necessary to approach an object extremely in order to obtain a required resolution, and hence, it becomes impossible to achieve the object of the present invention.

Hence, according to the present invention, in the image pickup unit using a solid state color image pickup device in which color filter is arranged every pixel, it is desirable to use a solid state image pickup device which fulfills the conditional expression (1).

In addition, in an image pickup unit using a solid state image pickup device in which a luminance signal is generated every pixel, it is desirable to use a solid state image pickup device which fulfills the conditional expression (4).

On the other hand, the above-described conditional expression (2) and the conditional expression (5) specify a focal length of an objective optical system combined with a solid state image pickup device specified with the above-mentioned conditional expression (1) and the above-mentioned conditional expression (4).

As seen from the above-described expression (iv), as the focal length Fl of an objective optical system becomes large, a depth of field becomes shallow.

When Fl exceeds upper limits of the conditional expression (2) and conditional expression (5) as an objective optical system combined with the solid state image pickup device specified with the above-described conditional expression (1) and conditional expression (4), the depth of field becomes shallow, it becomes impossible to obtain a sufficient magnification or resolution power at a near point, or it becomes out of focus at a distant view, and hence, it becomes impossible to achieve the object of the present invention.

Next, lower limits of the conditional expression (2) and conditional expression (5) will be explained.

In an endoscope apparatus being equipped with an image pickup unit in which an image pickup plane of a solid state image pickup device is arranged near an image-formation plane of an objective optical system, and a circuit system which processes an image signal sent from the above-mentioned solid state image pickup device, when images of two points are formed on the image pickup plane of the solid state image pickup device through the objective optical system, a minimum distance on the solid state image pickup device on which two point images are resolved on an output signal from the above-mentioned circuit system is decided by a pixel pitch of the solid state image pickup device, and characteristics of the circuit system which processes an image signal sent from the solid state image pickup device. At this time, let a coefficient decided by the characteristics of the circuit system be K, and let the pixel pitch of the solid state image pickup device be P, and the above-mentioned minimum distance can be expressed as KP.

Generally, let a focal length of an optical system be Fl, and let a front focal position of the optical system be fF, and an image formation magnification $\beta$ of an object, which is arranged at an object distance X, by the optical system is as follows:

$$\beta = Fl/(X + fF) \quad (v)$$

Hence, the distance KP on an image pickup plane of a solid state image pickup device becomes KP/$\beta$ in an object side.

Since this shows to what degree of fineness of an object is resolved in an endoscope apparatus which is constructed of an image pickup unit equipped with a solid state image pickup device, and a circuit system which processes an image signal sent from the above-mentioned solid state image pickup device, when it is set as X=Xn (Xn: distance to near point of depth of field), it is exactly a resolution of the endoscope apparatus at the near point. When this value is set as R, R is expressed as follows:

$$R = KP \cdot (Xn + fF)/Fl \quad (vi)$$

From the expression (vi), when a value of the focal length Fl becomes small, a value of R becomes large.

When Fl exceeds lower limits of the conditional expression (2) and conditional expression (5) as the objective optical system with pixel pitch P combined with the solid state image pickup device specified with the above-described conditional expression (1) and conditional expression (4), it becomes impossible to observe a fine object since the value of the resolution R becomes too large at the nearest point Xn within the depth of field, making it impossible to achieve the object of the present invention.

Hence, in the image pickup unit using a solid state color image pickup device in which a color filter is arranged every pixel, it is desirable to use an objective optical system with a focus distance which fulfills the above-described conditional expression (2) to the pixel pitch P.

Further, in the image pickup unit using a solid state image pickup device in which a luminance signal is generated every pixel, it is desirable to use an objective optical system with a focus distance which fulfills the above-described conditional expression (5) to the pixel pitch P.

On the other hand, the above-described conditional expression (3) and the conditional expression (6) specify an effective f-number of an objective optical system combined with the solid state image pickup device specified with the above-mentioned conditional expression (1) and the above-mentioned conditional expression (4).

It is known that, in the case of forming an image with a lens, light is influenced by diffraction. A point image becomes large under an influence of diffraction as Fno. becomes larger, and when magnitude of this point image exceeds a certain limit, details of an object seem to be out of focus regardless of focusing efforts. This limit is specified by Rayleigh as a limitation distance in which two point images can be identified as separate images when they approach mutually, and with letting a wavelength of light be $\lambda$ and letting an effective f-number be Fno., it is expressed as $1.22 \cdot \lambda \cdot Fno$.

When Fno. exceeds upper limits of the conditional expressions in the combination of the solid state image pickup device specified by the above-described conditional expression (1) and conditional expression (4), and the objective optical system specified by the above-described conditional expression (2) and conditional expression (5), details of an object seem to be out of focus regardless of focusing efforts, and hence, it becomes impossible to achieve the object of the present invention.

As seen from the above-described expression (iv), as a value of Fno. becomes small, a depth of field becomes shallow.

When Fno. exceeds lower limits of the conditional expressions, in the combination of the solid state image pickup device specified with the above-described conditional expression (1) and conditional expression (4), and the objective optical system specified with the conditional expression (2) and conditional expression (5), a depth of field becomes shallow, it becomes impossible to obtain sufficient magnification or resolution power at a near point, or it becomes out of focus at a distant view, and hence, it becomes impossible to achieve the object of the present invention.

Hence, in the image pickup unit using a solid state color image pickup device in which a color filter is arranged every pixel, it is desirable to use an objective optical system with an effective f-number which fulfills the above-described conditional expression (3) to the pixel pitch P.

Also, in the image pickup unit using a solid state image pickup device in which a luminance signal is generated every pixel, it is desirable to use an objective optical system with an effective f-number which fulfills the above-described conditional expression (6) to the pixel pitch P.

In addition, since balance of a magnifying power and a resolution of an image pickup unit is good when it is constructed so that any one or all of the above-described conditional expression (1), conditional expression (2), and conditional expression (3) may fulfill the following conditional expression (1)', conditional expression (2)', and conditional expression (3)', it is further preferable.

$$390 < IH/P < 510 \quad \text{Conditional expression (1)'}$$

$$390 < Fl/P < 510 \quad \text{Conditional expression (2)'}$$

$$3000 \times P < Fno. < 4200 \times P \quad \text{Conditional expression (3)'}$$

Furthermore, since balance of a magnifying power and a resolution of an image pickup unit is good when it is constructed so that any one or all of the above-described conditional expression (4), conditional expression (5), and conditional expression (6) may fulfill the following conditional expression (4)', conditional expression (5)', and conditional expression (6)', it is further preferable.

$$260 < IH/P < 340 \quad \text{Conditional expression (4)'}$$

$$260 < Fl/P < 340 \quad \text{Conditional expression (5)'}$$

$$2000 \times P < \text{Fno.} < 2800 \times P \quad \text{Conditional expression (6)'}$$

Although it is indispensable that the endoscope according to the present invention is constructed of the solid state image pickup device and objective optical system which fulfill the above-mentioned conditions, it is necessary to also specify a position of an image pickup plane of the solid state image pickup device arranged near an image-formation plane of the objective optical system.

When the solid state color image pickup device in which a color filter is arranged every pixel is used, when an MTF on an optical axis in a spatial frequency 1/(3×P) is 10% or more, a diameter of a circle of confusion does not exceed a diameter of a permissible circle of confusion and it can be regarded as being within a depth of field, and hence, it is desirable to arrange the image pickup plane of the above-mentioned solid state image pickup device in a position where the image pickup plane of the solid state image pickup device and the optical axis of the objective optical system are perpendicular, and an MTF on the optical axis in a spatial frequency 1/(3×P) of the objective optical system at 4 mm of object distance, an MTF on the optical axis in the spatial frequency 1/(3×P) at 50 mm of object distance become 10% or more together.

Alternatively, when the solid state image pickup device in which a luminance signal is generated every pixel is used, when an MTF on the optical axis in a spatial frequency 1/(2×P) is 10% or more, a diameter of a circle of confusion does not exceed a diameter of a permissible circle of confusion and it can be regarded as being within a depth of field, and hence, it is desirable to arrange the image pickup plane of the above-mentioned solid state image pickup device in a position where the image pickup plane of the solid state image pickup device and the optical axis of the objective optical system are perpendicular, and an MTF on the optical axis in a spatial frequency 1/(2×P) of an objective optical system at 4 mm of object distance, an MTF on the optical axis in the spatial frequency 1/(2×P) at 50 mm of object distance become 10% or more together.

Alternatively, the endoscope according to the present invention is constructed by combination of the solid state color image pickup device in which a color filter is arranged every pixel, and the objective optical system, satisfying the above-described conditional expression (1), conditional expression (2), and conditional expression (3), or combination of the solid state image pickup device in which a luminance signal is generated every pixel, and an objective optical system, satisfying the above-described conditional expression (4), conditional expression (5), and conditional expression (6), wherein an image pickup plane of the solid state image pickup device and the optical axis of the objective optical system are perpendicular, and with letting a range in an object side, where a resolution power on the optical axis (image center) is 25 lines/mm or more, be d1, and letting a range in the object side, where a resolution power on the optical axis (image center) is 2 lines/mm or more, be d2, it is desirable to arrange the image pickup plane of the above-mentioned solid state image pickup device in such a position that an object point which is in a position apart by 3.5 mm from an end surface of the objective optical system on the optical axis is included in both of d1 and d2, and an object point which is at a position apart by 50 mm from the end surface of the objective optical system on the optical axis is included only in d2.

Since it becomes possible to observe fine structure of living body tissues such as a large intestine pit pattern, for example, in the endoscope apparatus for medical use by arranging the image pickup plane of the solid state image pickup device so that an object point in a position apart by 3.5 mm may be included in a range (d2) in an object side where a resolution power is 2 lines/mm or more, and may be included in a range (d1) in the object side where a resolution power is 25 lines/mm or more, it is useful when performing an accurate diagnosis and treatment of a lesion section.

Furthermore, since it is possible to obtain a clear image also when observing a distant view by an object point in the position apart by 50 mm being included within a range (d2) in an object side in which a resolution power is 2 lines/mm or more, it is possible not only to perform screening with observing an interior space of an organism broadly, but also to easily perform an operation of guiding an end of an endoscope insertion section to a position to be observed.

Alternatively, the endoscope according to the present invention is constructed by combination of the solid state color image pickup device in which a color filter is arranged every pixel, and the objective optical system, satisfying the above-described conditional expression (1), conditional expression (2), and conditional expression (3), or combination of the solid state image pickup device in which a luminance signal is generated every pixel, and an objective optical system, satisfying the above-described conditional expression (4), conditional expression (5), and conditional expression (6), wherein an image pickup plane of the solid state image pickup device and the optical axis of the objective optical system are perpendicular, and it is desirable to arrange the image pickup plane of the above-mentioned solid state image pickup device in such a position that has a resolution of 35 μm or more when an object distance is 4 mm, and has a resolution of 0.45 mm or more when the object distance is 50 mm.

Since it becomes possible to observe fine structure of living body tissues such as a large intestine pit pattern, for example, in the endoscope apparatus for medical use by having a resolution of 35 μm or more at 4 mm of object distance, it is useful when performing an accurate diagnosis and treatment of a lesion section.

Furthermore, since it is possible to obtain a clear image also when observing a distant view by having a resolution of 0.45 mm or more at an object distance of 50 mm, it is possible not only to perform screening with observing an interior space of an organism broadly, but also to easily perform an operation of guiding an end of an endoscope insertion section to a position to be observed.

It is possible to obtain a clear image, since the unit a large depth of field continuously from a distant view to a near point, and has a high resolution at a distance of 3 to 4 mm at which it is easy to use, by arranging an objective optical system and a solid state image pickup device in the above-mentioned form.

In addition, by arranging an image pickup unit and a channel for treatment so that at least a part of treatment tool may enter within a visual field of the image pickup unit when protruding the treatment tool such as biopsy forceps through the channel for treatment from an end of an endoscope insertion section to a distance of 4 mm, it becomes possible to perform sampling of a tissue, or the like with observing fine structure of the living body tissue. Thereby, it is possible to increase treatment accuracy of a lesion section.

The endoscope according to the present invention has the following effects by having the above construction.

- Easy insertion of a scope and screening because of a distant view being observable
- Capability of smooth approach to a position on which to perform enlarged observation, because of a distant view being observable
- Capability of obtaining an enlarged image which has a high resolution at a distance of 3 to 4 mm at which it is easy to use
- Capability of keeping an object in view because of a distant view side being continuously within a depth of field at the time of enlarged observation
- Easy operation because of a complicated operation such as zooming, or the like being unnecessary
- Being able to construct an outer diameter of an insertion section finely because of no movable part being in an image pickup unit
- Capability of suppressing manufacturing cost because of no movable part being in the image pickup unit
- Capability of performing high-precision treatment because of a treatment tool entering within a visual field with observing an enlarged image The Advantages of the present invention will become more apparent upon reading the following detailed description in conjunction with the accompanying drawings.

DETAILED DESCRIPTION OF THE PREFERRED EMBODIMENT(S)

As embodiments of an endoscope of the present invention, data of objective optical systems and data of solid state image pickup devices will be shown. However, IH denotes a maximum image height, P denotes a pixel pitch of a solid state image pickup device, Fl denotes a focal length of an objective optical system, Fno. denotes an opening ratio, $2\omega$ denotes an angle of visibility, R denotes a radius of curvature of each lens surface, D denotes a thickness and a lens gap of each lens, and Ne denotes a refractive index in an e-line, and Vd denotes an Abbe number.

In addition, data of two examples will be shown below as objective optical systems and solid state image pickup devices of conventional endoscopes for comparison.

CONVENTIONAL EXAMPLE 1

Solid state image pickup device which generates a luminance signal every pixel:

IH=0.76 mm P=0.0044 mm IH/P=173

Objective Optical System:

| Fl = 0.77698 mm Fno. = 6.457 $2\omega$ = 133.6° | | | | |
|---|---|---|---|---|
| Fl/P = 177 1600 × P = 6.4 2800 × P = 11.2 | | | | |
| Surface No. | R | D | Ne | Vd |
| 1 | ∞ | 0.30 | 1.88814 | 40.8 |
| 2 | 0.523 | 0.31 | | |
| 3 | ∞ | 0.30 | 1.51825 | 64.1 |
| 4 | ∞ | 0.17 | | |
| 5 | 2.962 | 0.97 | 1.73234 | 54.7 |
| 6 | −1.102 | 0.08 | | |
| 7 | ∞ (aperture) | 0.03 | | |
| 8 | ∞ | 0.50 | 1.51563 | 75.0 |
| 9 | ∞ | 0.15 | | |
| 10 | 2.610 | 0.88 | 1.73234 | 54.7 |
| 11 | −0.812 | 0.23 | 1.85504 | 23.8 |
| 12 | −7.637 | 0.38 | | |
| 13 | ∞ | 0.75 | 1.51825 | 64.2 |
| 14 | ∞ | 0.01 | 1.5119 | 64.1 |
| 15 | ∞ | 0.60 | 1.52194 | 64.1 |
| 16 | ∞ | 0.00 | | |

Figure 16:
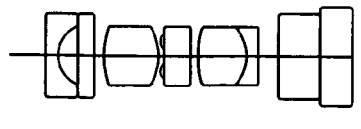
FIG. 16 is a sectional view of an objective optical system of a first conventional example.

FIG. 16 is a sectional view of an objective optical system of a first conventional example.

The first conventional example is an example of a conventional endoscope apparatus using a solid state image pickup device in which a luminance signal is generated every pixel.

A highest resolution power is 24 lines/mm at 3.0 mm of object distance, and does not have a range in which a resolution power becomes 25 lines/mm or more. A range in an object side, where the resolution power on the optical axis is 2 lines/mm or more, is 0 to 33 mm.

In addition, the resolution at the time of 4 mm of object distance is 49 µm, and the resolution at the time of 50 mm of object distance is 0.57 mm. A depth of field is 3.0 mm to infinity (∞)

The first conventional example is a case of being less than a range by the conditional expression (4) and conditional expression (5). In this case, although a large depth of field can be taken, when comparing in the same object distance, a resolution becomes lower than that of the endoscope apparatus according to the present invention.

Although it is possible to obtain a higher resolution by further enlarging Fno. to further extend the depth of field in the near point side, and further approaching an object, it becomes difficult to handle it since a distance from the object becomes near too much at that time. In addition, at the time of enlarged observation, a treatment tool does not enter within a visual field.

CONVENTIONAL EXAMPLE 2

Solid state color image pickup device in which a color filter is arranged every pixel:
IH=1.24 mm P=0.00205 mm IH/P=605
Objective Optical System:

| Fl = 1.29838 mm Fno. = 8.532 2ω = 141.6° | | | |
|---|---|---|---|
| Fl/P = 633 2400 × P = 5.28 4200 × P = 9.24 | | | |
| Surface No. | R | D | Ne | Vd |
| 1 | ∞ | 0.47 | 1.51825 | 64.1 |
| 2 | 0.951 | 0.14 | | |
| 3 | ∞ (aperture) | 0.03 | | |
| 4 | −2.880 | 1.07 | 1.69979 | 55.5 |
| 5 | −0.844 | 0.05 | | |
| 6 | 3.225 | 0.67 | 1.69979 | 55.5 |
| 7 | −1.551 | 0.28 | 1.93305 | 21.3 |
| 8 | −11.120 | 0.43 | | |
| 9 | ∞ | 0.90 | 1.52591 | 65.6 |
| 10 | ∞ | 0.50 | 1.53211 | 60.0 |
| 11 | ∞ | 0.40 | 1.5432 | 40.0 |
| 12 | ∞ | 0.00 | | |

Figure 17:
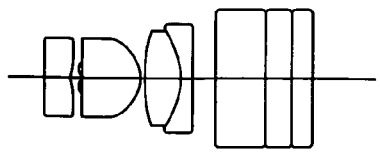
FIG. 17 is a sectional view of an objective optical system of a second conventional example.

FIG. 17 is a sectional view of an objective optical system of a second conventional example.

The second conventional example is an example of a conventional endoscope apparatus using a solid state image pickup device in which a luminance signal is generated every pixel.

A range in an object side, where the resolution power on the optical axis is 25 lines/mm or more, is 5.8 to 8.0 mm, and a range in an object side, where the resolution power on the optical axis is 2 lines/mm or more, is 0 to 100 mm. In addition, an object distance of 4 mm is out of a depth of field. A resolution in the case of an object distance of 50 mm is 0.25 mm. The depth of field is 6.5 to 50 mm.

The second conventional example is a case of being more than a range by the above-mentioned conditional expression (1) and conditional expression (2). Although a resolution becomes higher than that of the endoscope according to the present invention in comparison in the same object distance, since the depth of field becomes shallow, it becomes out of focus when approaching an object.

When Fno. is enlarged further, magnitude of a diffraction image by the objective optical system exceeds the permissible circle of confusion of the solid state image pickup device, and hence, contrast of an image in the depth of field drops.

Hence, even if there is a position which it is intended to see enlargingly, it becomes out of focus when trying to approach it, and hence, it is not possible to achieve the object of the present invention.

Next, data of embodiments of the present invention will be shown.

Embodiment 1

Solid state color image pickup device in which a color filter is arranged every pixel:
IH=1.442 mm P=0.003 mm IH/P=481
Objective Optical System:

| Fl = 1.47866 mm Fno. = 11.710 2ω = 132.3° | | | |
|---|---|---|---|
| Fl/P = 493 2400 × P = 7.2 4200 × P = 12.6 | | | |
| Surface No. | R | D | Ne | Vd |
| 1 | ∞ | 0.40 | 1.88814 | 40.8 |
| 2 | 1.080 | 0.62 | | |
| 3 | ∞ | 0.43 | 1.52498 | 59.9 |
| 4 | ∞ | 0.25 | | |
| 5 | 5.261 | 2.19 | 1.79196 | 47.4 |
| 6 | −2.733 | 0.03 | | |
| 7 | ∞ (aperture) | 0.03 | | |
| 8 | ∞ | 0.60 | 1.51965 | 75.0 |
| 9 | ∞ | 1.14 | | |
| 10 | 4.500 | 1.60 | 1.73234 | 54.7 |
| 11 | −1.870 | 0.43 | 1.93429 | 18.9 |
| 12 | −5.513 | 1.35 | | |
| 13 | ∞ | 1.00 | 1.51825 | 64.1 |
| 14 | ∞ | 0.01 | 1.51193 | 63.0 |
| 15 | ∞ | 1.00 | 1.6135 | 50.2 |
| 16 | ∞ | 0.00 | | |

Figure 1:
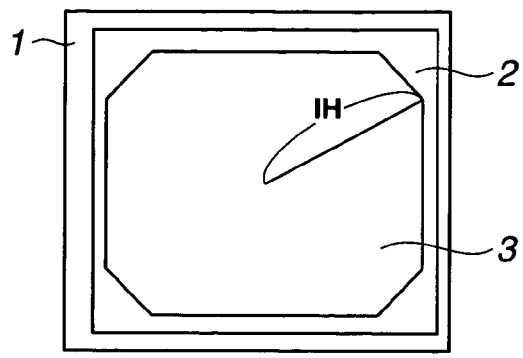
FIG. 1 is an explanatory diagram of a display area of a solid state image pickup device.
Figure 2:
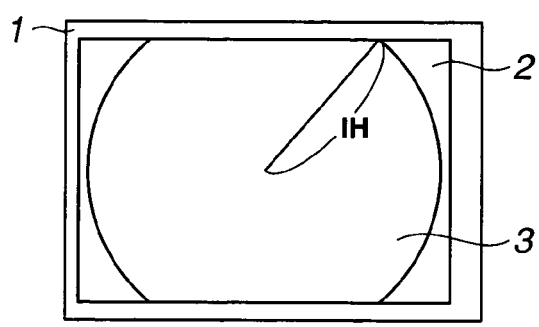
FIG. 2 is an explanatory diagram of a display area of another solid state image pickup device.
Figure 3:
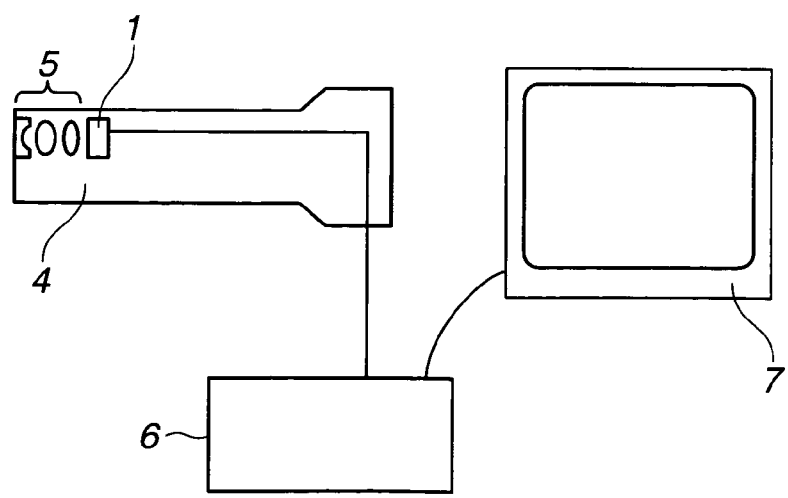
FIG. 3 is a conceptual diagram of construction of an endoscope apparatus.
Figure 4:
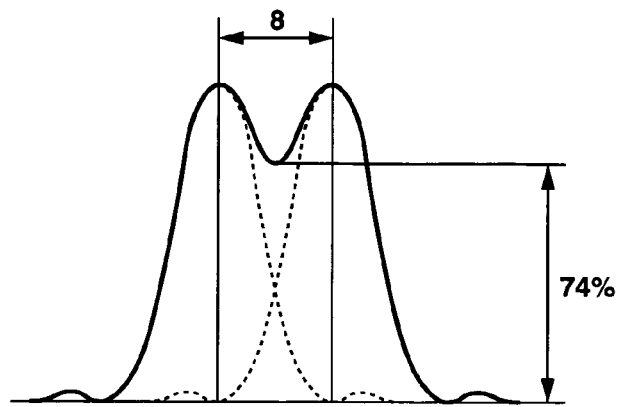
FIG. 4 is an explanatory diagram of a definition of a resolution.
Figure 5:
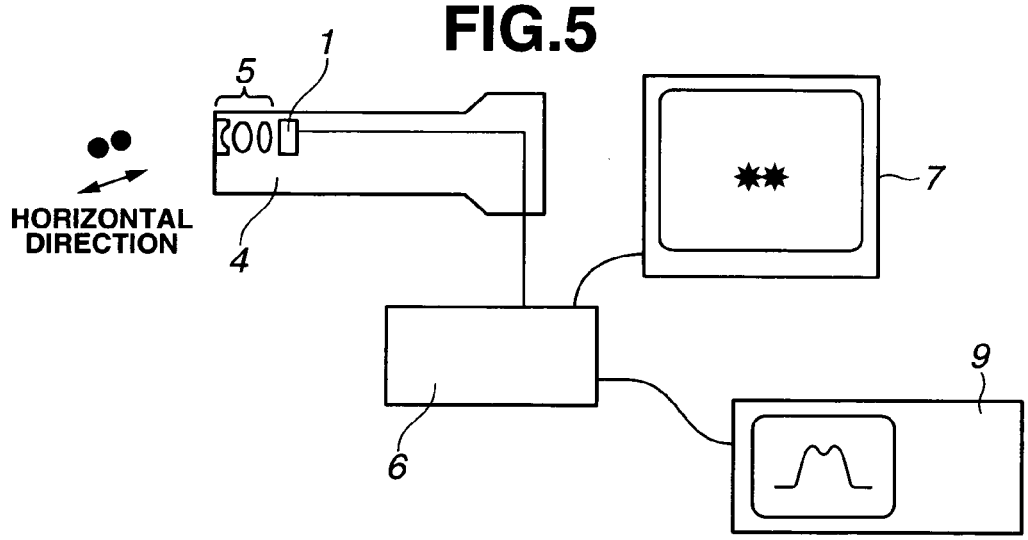
FIG. 5 is an explanatory diagram of a measuring method of the resolution.
Figure 6:
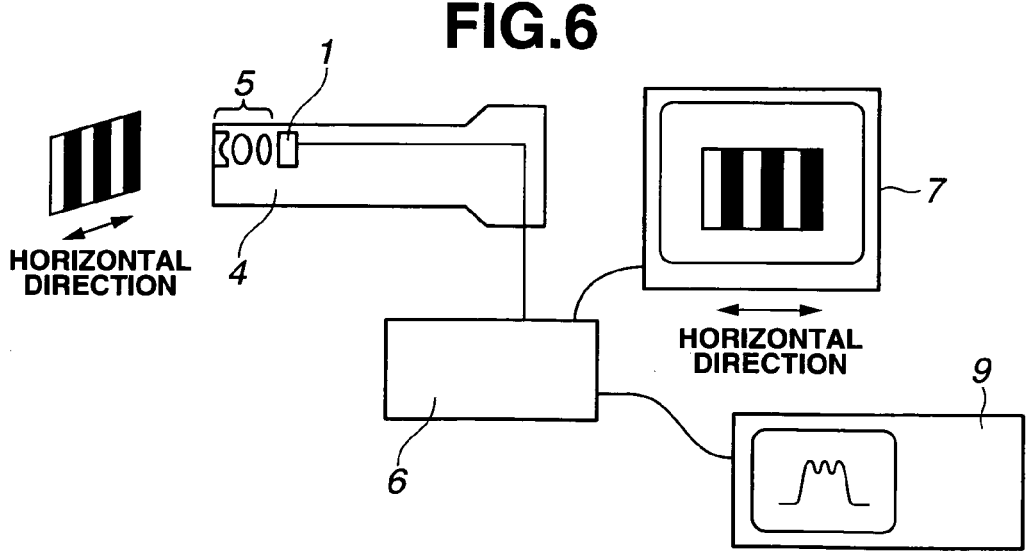
FIG. 6 is an explanatory diagram of another measuring method of the resolution.
Figure 7:
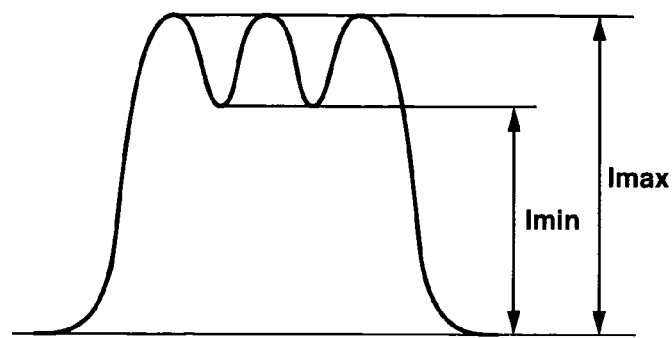
FIG. 7 is an explanatory diagram of a definition of a resolution power.
Figure 8:
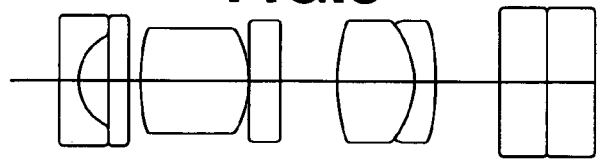
FIG. 8 is a sectional view of an objective optical system of a first embodiment of the present invention.
Figure 9:
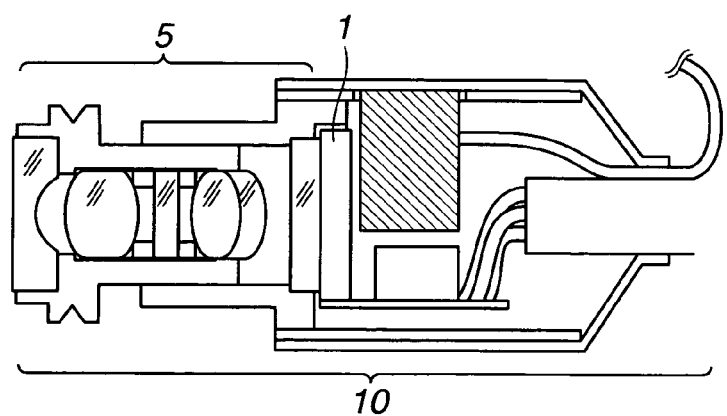
FIG. 9 is a sectional view of an image pickup unit of the first embodiment of the present invention.

FIG. 8 shows a sectional view of an objective optical system of a first embodiment.

The first embodiment is an embodiment of an endoscope apparatus for medical use using a solid state color image pickup device in which a color filter is arranged every pixel.

An MTF on an optical axis in a spatial frequency $1/(3\times P)$ at 4 mm of object distance is 12.6%, and an MTF on the optical axis in the spatial frequency $1/(3\times P)$ at 50 mm of object distance is 10.8%.

A range in an object side, where the resolution power on the optical axis is 25 lines/mm or more, is 3.2 to 5.5 mm, and a range in the object side, where the resolution power on the optical axis is 2 lines/mm or more, is 0 to 80 mm.

In addition, the resolution at the time of 4 mm of object distance is 29 μm, and the resolution at the time of 50 mm of object distance is 0.31 mm.

Hence, the endoscope apparatus according to the first embodiment fulfills the following conditions.

That is, the endoscope apparatus is equipped with a fixed focus image pickup unit which is constructed of an objective optical system, and a solid state color image pickup device in which a color filter is arranged every pixel, the solid state image pickup device fulfills a conditional expression (1), the objective optical system fulfills a conditional expression (2) and a conditional expression (3), and an image pickup plane of the solid state image pickup device is arranged in a position where an MTF on an optical axis in a spatial frequency $1/(3\times P)$ of the objective optical system at 4 mm of object distance, and an MTF on the optical axis in the spatial frequency 1/(3×P) at 50 mm of object distance become 10% or more together.

$300 < IH/P < 550$   Conditional expression (1)

$300 < Fl/P < 550$   Conditional expression (2)

$2400 \times P < Fno. < 4200 \times P$   Conditional expression (3)

where

P: horizontal pixel pitch [mm] of solid state image pickup device

IH: distance [mm] to most distant position from center in display area of solid state image pickup device Fl: focal length [mm] of objective optical system Fno.: effective f-number of objective optical system In addition, the endoscope apparatus according to the first embodiment fulfills the following conditions.

That is, in the endoscope apparatus equipped with an endoscope which includes at least a fixed focus image pickup unit, and display means which displays an image which the image pickup unit acquires, the image pickup unit is constructed of a solid state image pickup device in which a color filter is arranged every pixel and which fulfills the above-mentioned conditional expression (1), and an objective optical system which fulfills the above-mentioned conditional expression (2), and the above-mentioned conditional expression (3), and with letting a range of the image pickup unit in an object side, where a resolution in a center of an image displayed on the display means is 25 lines/mm or more, be d1, and letting a range of the image pickup unit in an object side, where a resolution in a center of an image displayed on the display means is 2 lines/mm or more, be d2, an image pickup plane of the solid state image pickup device is arranged near an image forming position of an objective optical system so that an object point on the optical axis which is at a position apart by 3.5 mm from a plane of the objective optical system in a side nearest to the object which constructs an image pickup unit may be included in both of d1 and d2, and so that an object point on the optical axis which is at a position apart by 50 mm from a plane of the objective optical system in a side nearest to the object which constructs the image pickup unit may be included in only d2.

$300 < IH/P < 550$   Conditional expression (1)

$300 < Fl/P < 550$   Conditional expression (2)

$2400 \times P < Fno. < 4200 \times P$   Conditional expression (3)

where

P: horizontal pixel pitch [mm] of solid state image pickup device

IH: distance [mm] to most distant position from center in display area of solid state image pickup device Fl: focal length [mm] of objective optical system Fno.: effective f-number of objective optical system In addition, the endoscope apparatus according to the first embodiment fulfills the following conditions.

That is, in an endoscope apparatus which is equipped with a fixed focus image pickup unit which forms an objective image with an objective optical system, and which acquires an image signal with a solid state image pickup device in which a color filter is arranged every pixel near an image-formation plane of the objective optical system, and a circuit system which processes the image signal sent from the solid state image pickup device, the solid state image pickup device fulfills a conditional expression (1), the objective optical system fulfills a conditional expression (2) and a conditional expression (3), and this has a resolution of 35 µm or more when a distance from the objective optical system to an object is 4 mm, and has a resolution of 0.45 mm or more when the distance from the objective optical system to the object is 50 mm.

$300 < IH/P < 550$   Conditional expression (1)

$300 < Fl/P < 550$   Conditional expression (2)

$2400 \times P < Fno. < 4200 \times P$   Conditional expression (3)

where

P: horizontal pixel pitch [mm] of solid state image pickup device

Figure 10:
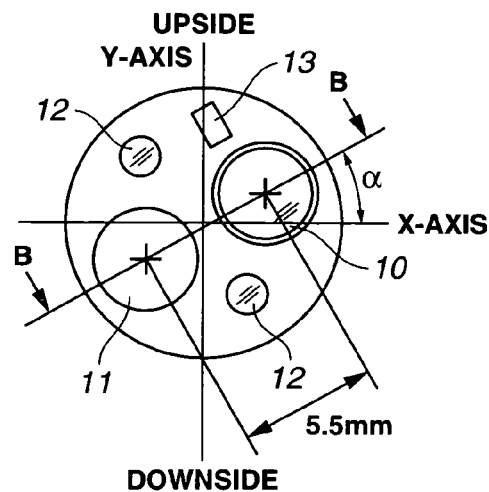
FIG. 10 is a diagram of an endoscope insertion section of the first embodiment of the present invention in view of its end.
Figure 11:
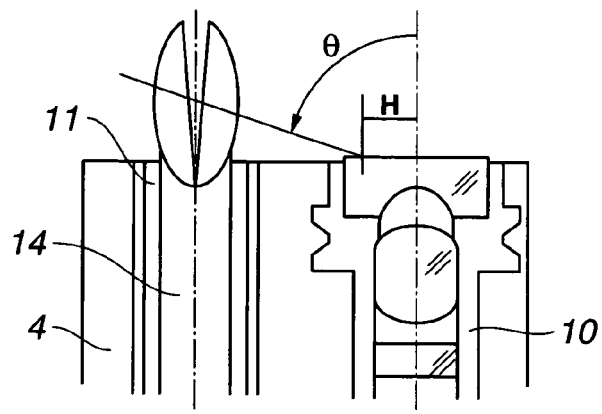
FIG. 11 is a sectional view of the endoscope insertion section of the first embodiment of the present invention.

IH: distance [mm] to most distant position from center in display area of solid state image pickup device Fl: focal length [mm] of objective optical system Fno.: effective f-number of objective optical system In addition, an endoscope end portion has structure as shown in FIGS. 10 and 11.

FIG. 10 is a front view of an end surface of the endoscope insertion section, and FIG. 11 is a sectional view taken on line B-B in FIG. 10.

A center of a channel for treatment is arranged at a position apart by 5.5 mm from the optical axis of the image pickup unit in a direction of 300 lower right of an image pickup unit 10 (in FIG. 10, lower left α=30°) toward an object from the end surface of the endoscope insertion section. Since a half angle of view θ in this direction is 59.2° and a ray height H of a first lens surface (most front surface in an object side) of the objective optical system is 1.01 mm, when a treatment tool is protruded by 2.68 mm or more, an treatment tool end enters into a visual field range. Hence, hereby, the endoscope apparatus according to the first embodiment fulfills the following conditions.

That is, in the endoscope equipped with the fixed focus image pickup unit, the endoscope insertion section is further equipped with a treatment tool insertion channel, and the above-mentioned image pickup unit and the above-mentioned treatment tool insertion channel are arranged so that at least a part of the treatment tool may enter within the visual field of an image pickup unit when a treatment tool is protruded through the channel for treatment from the endoscope insertion section end by 4 mm of distance.

In the endoscope apparatus according to the first embodiment, a far point side of a depth of field is 60 mm and a near point side of the depth of field is 3.7 mm.

In a distant view, it has sufficient performance for insertion into a body and screening of a lesion section. In addition, in the near point side, since it has a resolution of 28 µm at 3.7 mm, it is possible to perform enlarged observation of a large intestine pit pattern and the like.

At this time, since the distant view side is in a depth of field continuously, there are features of not only that it is possible to smoothly approach a position which it is intended to enlarging observe, but also that it is hard to miss an object.

Furthermore, since a zooming operation of such an endoscope equipped with a zoom image pickup unit is unnecessary, an operation of the scope is easy.

In addition, since there is no movable part in the image pickup unit, in comparison with an endoscope equipped with an zoom image pickup unit, an outer diameter of the insertion section is small, and hence, it is also possible to suppress manufacturing cost low. Furthermore, it is possible to perform high-precision treatment because a treatment tool enters in a visual field with observing an enlarged image.

Moreover, the first embodiment fulfills also the conditional expression (1)', conditional expression (2)', and conditional expression (3)'.

In this way, the endoscope according to the first embodiment has a resolution of 28 μm at 3.7 mm of object distance, and, at this time, let a horizontal width of a display area of the solid state image pickup device be 2.4 mm and let a horizontal width of an image displayed on a monitor be 320 mm, a magnification on the monitor becomes 45 times, and balance of a working distance, a resolution, and a magnification becomes excellent, and hence, it is further preferable.

Embodiment 2

Solid state color image pickup device in which a color filter is arranged every pixel:
IH=1.676 mm P=0.0035 mm IH/P=479
Objective Optical System:

Fl = 1.58676 mm Fno. = 12.965 2ω = 162.6°
Fl/P = 453 2400 × P = 8.4 4200 × P = 14.7

| Surface No. | R | D | Ne | Vd |
|---|---|---|---|---|
| 1 | ∞ | 0.50 | 1.88814 | 40.8 |
| 2 | 1.260 | 0.78 | | |
| 3 | ∞ | 0.50 | 1.52498 | 59.9 |
| 4 | ∞ | 0.35 | | |
| 5 | 7.625 | 2.65 | 1.79196 | 47.4 |
| 6 | −2.820 | 0.04 | | |
| 7 | ∞ (aperture) | 0.03 | | |
| 8 | ∞ | 0.75 | 1.51965 | 75.0 |
| 9 | ∞ | 1.45 | | |
| 10 | 4.878 | 1.78 | 1.73234 | 54.7 |
| 11 | −2.485 | 0.50 | 1.93429 | 18.9 |
| 12 | −9.120 | 1.15 | | |
| 13 | ∞ | 1.20 | 1.51825 | 64.1 |
| 14 | ∞ | 0.01 | 1.51193 | 63.0 |
| 15 | ∞ | 1.00 | 1.61379 | 50.2 |
| 16 | ∞ | 0.00 | | |

Figure 12:
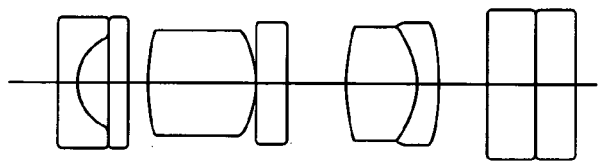
FIG. 12 is a sectional view of an objective optical system of a second embodiment of the present invention.

FIG. 12 shows a sectional view of an objective optical system of a second embodiment.

The second embodiment is an embodiment of an endoscope apparatus using a solid state color image pickup device in which a color filter is arranged every pixel.

An MTF on an optical axis in a spatial frequency $1/(3\times P)$ in 4 mm of object distance is 15.4%, and an MTF on the optical axis in the spatial frequency $1/(3\times P)$ in 50 mm of object distance is 13.9%.

A range in an object side, where the resolution power on the optical axis is 25 lines/mm or more, is 2.9 to 4.9 mm, and a range in an object side, where the resolution power on the optical axis is 2 lines/mm or more, is 0 to 80 mm.

In addition, the resolution at the time of 4 mm of object distance is 32 μm, and the resolution at the time of 50 mm of object distance is 0.34 mm.

Hence, the endoscope apparatus according to the second embodiment fulfills the following conditions.

That is, the endoscope apparatus is equipped with a fixed focus image pickup unit which is constructed of an objective optical system, and a solid state color image pickup device in which a color filter is arranged every pixel, the solid state image pickup device fulfills a conditional expression (1), the objective optical system fulfills a conditional expression (2) and a conditional expression (3), and an image pickup plane of the solid state image pickup device is arranged in a position where an MTF on an optical axis in a spatial frequency $1/(3\times P)$ of the objective optical system in 4 mm of object distance, and an MTF on the optical axis in the spatial frequency $1/(3\times P)$ in 50 mm of object distance become 10% or more together.

$300 < IH/P < 550$      Conditional expression (1)

$300 < Fl/P < 550$      Conditional expression (2)

$2400 \times P < Fno. < 4200 \times P$      Conditional expression (3)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system In addition, the endoscope apparatus according to the second embodiment fulfills the following conditions.

That is, in the endoscope apparatus equipped with an endoscope which includes at least a fixed focus image pickup unit, and display means which displays an image which the image pickup unit acquires, the image pickup unit is constructed of a solid state image pickup device in which a color filter is arranged every pixel and which fulfills the above-mentioned conditional expression (1), and an objective optical system which fulfills the above-mentioned conditional expression (2), and the above-mentioned conditional expression (3), and with letting a range of the image pickup unit in an object side, where a resolution in a center of an image displayed on the display means is 25 lines/mm or more, be d1, and letting a range of the image pickup unit in an object side, where a resolution in a center of an image displayed on the display means is 2 lines/mm or more, be d2, an image pickup plane of the solid state image pickup device is arranged near an image forming position of an objective optical system so that an object point on the optical axis which is at a position apart by 3.5 mm from a plane of the objective optical system in a side nearest to the object which constructs an image pickup unit may be included in both of d1 and d2, and so that an object point on the optical axis which is at a position apart by 50 mm from a plane of the objective optical system in a side nearest to the object which constructs the image pickup unit may be included in only d2.

$300 < IH/P < 550$      Conditional expression (1)

$300 < Fl/P < 550$      Conditional expression (2)

$2400 \times P < Fno. < 4200 \times P$      Conditional expression (3)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system In addition, the endoscope apparatus according to the second embodiment fulfills the following conditions.

That is, in an endoscope apparatus which is equipped with a fixed focus image pickup unit which forms an objective image with an objective optical system, and which acquires an image signal with a solid state image pickup device in which a color filter is arranged every pixel near an image-formation plane of the objective optical system, and a circuit system which processes the image signal sent from the solid state image pickup device, the solid state image pickup device fulfills a conditional expression (1), the objective optical system fulfills a conditional expression (2) and a conditional expression (3), and this has a resolution of 35 µm or more when a distance from the objective optical system to an object is 4 mm, and has a resolution of 0.45 mm or more when the distance from the objective optical system to the object is 50 mm.

300<IH/P<550      Conditional expression (1)

300<Fl/P<550      Conditional expression (2)

2400×P<Fno.<4200×P      Conditional expression (3)

where

P: horizontal pixel pitch [mm] of solid state image pickup device

IH: distance [mm] to most distant position from center in display area of solid state image pickup device Fl: focal length [mm] of objective optical system Fno.: effective f-number of objective optical system The second embodiment has an angle of visibility of 162.6° and has a feature that a wide range is observable at once. Hence, when it is used as, for example, a medical use endoscope apparatus, it is suitable for screening of a lesion section since it has a large visual field in a distant view, and further, since it is possible to have a resolution of 28 µm at 3.2 mm, it is possible to construct endoscope apparatus which can perform enlarged observation of a large intestine pit pattern, and the like.

Embodiment 3

Solid state color image pickup device in which a color filter is arranged every pixel:
IH=1.3 mm P=0.0025 mm IH/P=520
Objective Optical System:

| Fl = 1.33785 mm Fno. = 10.003 2ω = 132.1° | | | | |
| Fl/P = 535 2400 × P = 6.0 4200 × P = 10.5 | | | | |
| Surface No. | R | D | Ne | Vd |
| --- | --- | --- | --- | --- |
| 1 | ∞ | 0.40 | 1.77067 | 71.7 |
| 2 | 0.977 | 0.57 | | |
| 3 | ∞ | 0.40 | 1.52498 | 59.9 |
| 4 | ∞ | 0.84 | | |
| 5 | ∞ (aperture) | 0.03 | | |
| 6 | ∞ | 1.90 | 1.81078 | 40.9 |
| 7 | −2.192 | 0.10 | | |
| 8 | 3.168 | 1.68 | 1.51825 | 64.1 |
| 9 | −1.676 | 0.39 | 1.93429 | 18.9 |
| 10 | −5.048 | 0.10 | | |
| 11 | ∞ | 0.60 | 1.51965 | 75.0 |
| 12 | ∞ | 1.16 | | |
| 13 | ∞ | 1.00 | 1.51825 | 64.1 |
| 14 | ∞ | 0.03 | 1.5119 | 64.1 |
| 15 | ∞ | 1.00 | 1.61379 | 50.2 |
| 16 | ∞ | 0.00 | | |

Figure 13:
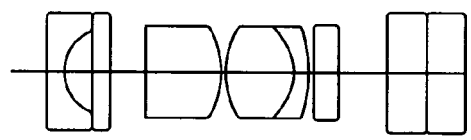
FIG. 13 is a sectional view of an objective optical system of a third embodiment of the present invention.

FIG. 13 shows a sectional view of an objective optical system of a third embodiment.

The third embodiment is an embodiment of an endoscope apparatus using a solid state color image pickup device in which a color filter is arranged every pixel.

An MTF on an optical axis in a spatial frequency 1/(3×P) at 4 mm of object distance is 9.2%. An MTF on an optical axis in the spatial frequency 1/(3×P) at 50 mm of object distance is 10.6%.

A range in an object side, where a resolution power on the optical axis is 25 lines/mm or more, is 3.7 to 6.0 mm, and a range in an object side, where the resolution power on the optical axis is 2 lines/mm or more, is 0 to 85 mm.

In addition, the resolution at the time of 4 mm of object distance is 30 µm, and the resolution at the time of 50 mm of object distance is 0.28 mm.

Hence, the endoscope apparatus according to the third embodiment fulfills the following conditions.

That is, in an endoscope apparatus which is equipped with a fixed focus image pickup unit which forms an objective image with an objective optical system, and which acquires an image signal with a solid state image pickup device in which a color filter is arranged every pixel near an image-formation plane of the objective optical system, and a circuit system which processes the image signal sent from the solid state image pickup device, the solid state image pickup device fulfills a conditional expression (1), the objective optical system fulfills a conditional expression (2) and a conditional expression (3), and this has a resolution of 35 µm or more when a distance from the objective optical system to an object is 4 mm, and has a resolution of 0.45 mm or more when the distance from the objective optical system to the object is 50 mm.

300<IH/P<550      Conditional expression (1)

300<Fl/P<550      Conditional expression (2)

2400×P<Fno.<4200×P      Conditional expression (3)

where

P: horizontal pixel pitch [mm] of solid state image pickup device

IH: distance [mm] to most distant position from center in display area of solid state image pickup device Fl: focal length [mm] of objective optical system Fno.: effective f-number of objective optical system The third embodiment is an example that respective parameters of IH/P, Fl/P, and Fno. are near upper limits within ranges specified in the above-described conditional expression (1), conditional expression (2), and conditional expression (3).

Although a depth of field in a near point side becomes 4.2 mm to become a little difficult to approach, it is possible to obtain a resolution of 27 µm at 4.2 mm, and hence, the endoscope apparatus according to the third embodiment can fulfill the object of the present invention fully. In addition, it has a feature that, since the solid state image pickup device has the comparatively large number of pixels, it is possible to obtain a highly detailed image.

Embodiment 4

Solid state color image pickup device in which a color filter is arranged every pixel:
IH=1.32 mm P=0.004 mm IH/P=330
Objective Optical System:

| Fl = 1.27394 mm Fno. = 10.326 2ω = 125.9° | | | | |
| Fl/P = 318 2400 × P = 9.6 4200 × P = 16.8 | | | | |
| Surface No. | R | D | Ne | Vd |
| --- | --- | --- | --- | --- |
| 1 | ∞ | 0.20 | 1.57392 | 53.0 |
| 2 | 0.422 | 0.21 | | |
| 3 | 2.189 | 0.49 | 1.81264 | 25.4 |
| 7 | ∞ (aperture) | 0.03 | | |
| 5 | ∞ | 0.60 | 1.48915 | 70.2 |

-continued

| Fl = 1.27394 mm Fno. = 10.326 2ω = 125.9° |
| Fl/P = 318  2400 × P = 9.6  4200 × P = 16.8 |

| Surface No. | R | D | Ne | Vd |
|---|---|---|---|---|
| 6 | −0.731 | 0.15 | | |
| 7 | ∞ | 0.63 | 1.54212 | 59.5 |
| 8 | −0.705 | 0.21 | 1.81264 | 25.4 |
| 9 | −1.342 | 0.82 | | |
| 10 | ∞ | 0.60 | 1.51825 | 64.1 |
| 11 | ∞ | 0.03 | | |
| 12 | ∞ | 1.80 | 1.51825 | 64.1 |
| 13 | ∞ | 0.00 | | |

Figure 14:
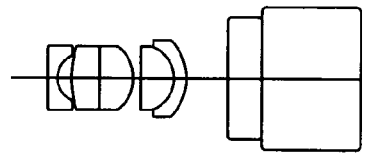
FIG. 14 is a sectional view of an objective optical system of a fourth embodiment of the present invention.

FIG. 14 shows a sectional view of an objective optical system of a fourth embodiment.

The fourth embodiment is an embodiment of an endoscope apparatus using a solid state color image pickup device in which a color filter is arranged every pixel.

An MTF on an optical axis in a spatial frequency 1/(3×P) in 4 mm of object distance is 24.8%, and an MTF on the optical axis in the spatial frequency 1/(3×P) in 50 mm of object distance is 11.5%.

A range in an object side, where a resolution power on the optical axis is 25 lines/mm or more, is 3.2 to 3.9 mm, and a range in the object side, where the resolution power on the optical axis is 2 lines/mm or more, is 0 to 55 mm.

In addition, a resolution at the time of 4 mm of object distance is 38 μm, and the resolution at the time of 50 mm of object distance is 0.47 mm.

Hence, the endoscope apparatus according to the fourth embodiment fulfills the following conditions.

That is, the endoscope apparatus is equipped with a fixed focus image pickup unit which is constructed of an objective optical system, and a solid state color image pickup device in which a color filter is arranged every pixel, the solid state image pickup device fulfills a conditional expression (1), the objective optical system fulfills a conditional expression (2) and a conditional expression (3), and an image pickup plane of the solid state image pickup device is arranged in a position where an MTF on an optical axis in a spatial frequency 1/(3×P) of the objective optical system in 4 mm of object distance, and an MTF on the optical axis in a spatial frequency 1/(3×P) in 50 mm of object distance become 10% or more together.

$300 < IH/P < 550$   Conditional expression (1)

$300 < Fl/P < 550$   Conditional expression (2)

$2400 \times P < Fno. < 4200 \times P$   Conditional expression (3)

where

P: horizontal pixel pitch [mm] of solid state image pickup device

IH: distance [mm] to most distant position from center in display area of solid state image pickup device Fl: focal length [mm] of objective optical system Fno.: effective f-number of objective optical system In addition, the endoscope apparatus according to the fourth embodiment fulfills the following conditions.

That is, in the endoscope apparatus equipped with an endoscope which includes at least a fixed focus image pickup unit, and display means which displays an image which the image pickup unit acquires, the image pickup unit is constructed of a solid state image pickup device in which a color filter is arranged every pixel and which fulfills a conditional expression (1), and an objective optical system which fulfills a conditional expression (2), and a conditional expression (3), and with letting a range of the image pickup unit in an object side, where a resolution in a center of an image displayed on the display means is 25 lines/mm or more, be d1, and letting a range of the image pickup unit in an object side, where a resolution in a center of an image displayed on the display means is 2 lines/mm or more, be d2, an image pickup plane of the solid state image pickup device is arranged near an image forming position of an objective optical system so that an object point on the optical axis which is at a position apart by 3.5 mm from a plane of the objective optical system in a side nearest to the object which constructs an image pickup unit may be included in both of d1 and d2, and so that an object point on the optical axis which is at a position apart by 50 mm from a plane of the objective optical system in a side nearest to the object which constructs the image pickup unit may be included in only d2.

$300 < IH/P < 550$   Conditional expression (1)

$300 < Fl/P < 550$   Conditional expression (2)

$2400 \times P < Fno. < 4200 \times P$   Conditional expression (3)

where

P: horizontal pixel pitch [mm] of solid state image pickup device

IH: distance [mm] to most distant position from center in display area of solid state image pickup device Fl: focal length [mm] of objective optical system Fno.: effective f-number of objective optical system The fourth embodiment is an example that respective parameters of IH/P, Fl/P, and Fno. are near lower limits within ranges specified in the above-described conditional expression (1), conditional expression (2), and conditional expression (3).

The endoscope apparatus according to the fourth embodiment has a resolution of 32 μm at 3.3 mm of object distance. Although a resolution becomes a little low in comparison with the case of fulfilling the above-described conditional expression (1)', conditional expression (2)', and conditional expression (3)', this can fulfill the object of the present invention fully.

In addition, since a solid state image pickup device with the comparatively few number of pixels can be used, this is advantageous at a point that it is easy to make an outer diameter of the endoscope insertion section small, to shorten a length of a rigid end, and the like.

Embodiment 5

Solid state image pickup device which generates a luminance signal every pixel:

IH=1.05 mm  P=0.0035 mm  IH/P=300

Objective Optical System:

| Fl = 1.04272 mm Fno. = 8.625 2ω = 133.7° |
| Fl/P = 298  1600 × P = 5.6  2800 × P = 9.8 |

| Surface No. | R | D | Ne | Vd |
|---|---|---|---|---|
| 1 | ∞ | 0.35 | 1.88814 | 40.8 |
| 2 | 0.557 | 0.50 | | |
| 3 | 2.469 | 1.14 | 1.73234 | 54.7 |
| 4 | −1.065 | 0.07 | | |
| 5 | ∞ (aperture) | 0.03 | | |

-continued

Fl = 1.04272 mm Fno. = 8.625 2ω = 133.7°
Fl/P = 298 1600 × P = 5.6 2800 × P = 9.8

| Surface No. | R | D | Ne | Vd |
|---|---|---|---|---|
| 6 | ∞ | 0.35 | 1.51563 | 75.0 |
| 7 | ∞ | 0.03 | | |
| 8 | ∞ | 0.35 | 1.51563 | 75.0 |
| 9 | ∞ | 0.32 | | |
| 10 | 3.740 | 0.80 | 1.72234 | 54.7 |
| 11 | −0.949 | 0.20 | 1.85504 | 23.8 |
| 12 | −9.773 | 0.48 | | |
| 13 | ∞ | 0.86 | 1.51825 | 64.1 |
| 14 | ∞ | 0.01 | 1.51193 | 63.0 |
| 15 | ∞ | 0.70 | 1.52207 | 60.0 |
| 16 | ∞ | 0.00 | | |

Figure 15:
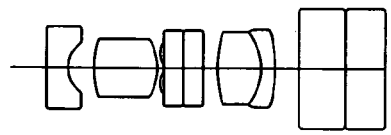
FIG. 15 is a sectional view of an objective optical system of, a fifth embodiment of the present invention.

FIG. 15 shows a sectional view of an objective optical system of a fifth embodiment.

The fifth embodiment is an embodiment of an endoscope apparatus using a solid state image pickup device in which a luminance signal is generated every pixel.

An MTF on an optical axis in a spatial frequency 1/(2×P) in 4 mm of object distance is 14.3%, and an MTF on the optical axis in the spatial frequency 1/(2×P) in 50 mm of object distance is 11.6%.

A range in an object side, where a resolution power on the optical axis is 25 lines/mm or more, is 3.2 to 5.5 mm, and a range in an object side, where the resolution power on the optical axis is 2 lines/mm or more, is 0 to 80 mm.

In addition, a resolution at the time of 4 mm of object distance is 29 μm, and the resolution at the time of 50 mm of object distance is 0.34 mm.

Hence, the endoscope apparatus according to the fifth embodiment fulfills the following conditions.

That is, the endoscope apparatus is equipped with a fixed focus image pickup unit which is constructed of an objective optical system, and a solid state image pickup device in which a luminance signal is generated every pixel, the solid state image pickup device fulfills a conditional expression (4), the objective optical system fulfills a conditional expression (5) and a conditional expression (6), and an image pickup plane of the solid state image pickup device is arranged in a position where an MTF on an optical axis in a spatial frequency 1/(2×P) of the objective optical system in 4 mm of object distance, and an MTF on the optical axis in the spatial frequency 1/(2×P) in 50 mm of object distance become 10% or more together.

200<IH/P<360      Conditional expression (4)

200<Fl/P<360      Conditional expression (5)

1600×P<Fno.<2800×P      Conditional expression (6)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system In addition, the endoscope apparatus according to the fifth embodiment fulfills the following conditions.

That is, in the endoscope apparatus equipped with an endoscope which includes at least a fixed focus image pickup unit, and display means which displays an image which the image pickup unit acquires, the image pickup unit is constructed of a solid state image pickup device in which a luminance signal is generated every pixel and which fulfills a conditional expression (4), and an objective optical system which fulfills a conditional expression (5), and a conditional expression (6), and with letting a range of the image pickup unit in an object side, where a resolution in a center of an image displayed on the display means is 25 lines/mm or more, be d1, and letting a range of the image pickup unit in an object side, where a resolution in a center of an image displayed on the display means is 2 lines/mm or more, be d2, an image pickup plane of the above-mentioned solid state image pickup device is arranged near an image forming position of an objective optical system so that an object point on the optical axis which is at a position apart by 3.5 mm from a plane of the objective optical system in a side nearest to the object which constructs an image pickup unit may be included in both of d1 and d2, and so that an object point on the optical axis which is at a position apart by 50 mm from a plane of the objective optical system in a side nearest to the object which constructs the image pickup unit may be included in only d2.

200<IH/P<360      Conditional expression (4)

200<Fl/P<360      Conditional expression (5)

1600×P<Fno.<2800×P      Conditional expression (6)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system In addition, the endoscope apparatus according to the fifth embodiment fulfills the following conditions.

That is, in an endoscope apparatus which is equipped with a fixed focus image pickup unit which forms an objective image with an objective optical system, and which acquires an image signal with a solid state image pickup device in which a luminance signal is generated every pixel near an image-formation plane of the objective optical system, and a circuit system which processes the image signal sent from the solid state image pickup device, the solid state image pickup device fulfills a conditional expression (4), the objective optical system fulfills a conditional expression (5) and a conditional expression (6), and this has a resolution of 35 μm or more when a distance from the objective optical system to an object is 4 mm, and has a resolution of 0.45 mm or more when the distance from the objective optical system to the object is 50 mm.

200<IH/P<360      Conditional expression (4)

200<Fl/P<360      Conditional expression (5)

1600×P<Fno.<2800×P      Conditional expression (6)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system Since using a solid state image pickup device in which a luminance signal is generated every pixel, the endoscope apparatus according to the fifth embodiment has a feature of being able to be easily used for special light observation such as fluorescence observation, infrared light observation, and narrow band light observation by devising illumination light or a filter inside an objective optical system.

In addition, since the endoscope apparatus according to the fifth embodiment uses the solid state image pickup device in which a luminance signal is generated every pixel, it is possible to construct an image pickup unit which has the fewer number of pixels but has the same specifications in comparison with an endoscope using a solid state color image pickup device in which a color filter is arranged every pixel. Hence, this is advantageous at a point that it is easy to make an outer diameter of the endoscope insertion section small, to shorten a length of a rigid end, and the like.

Figure 18:
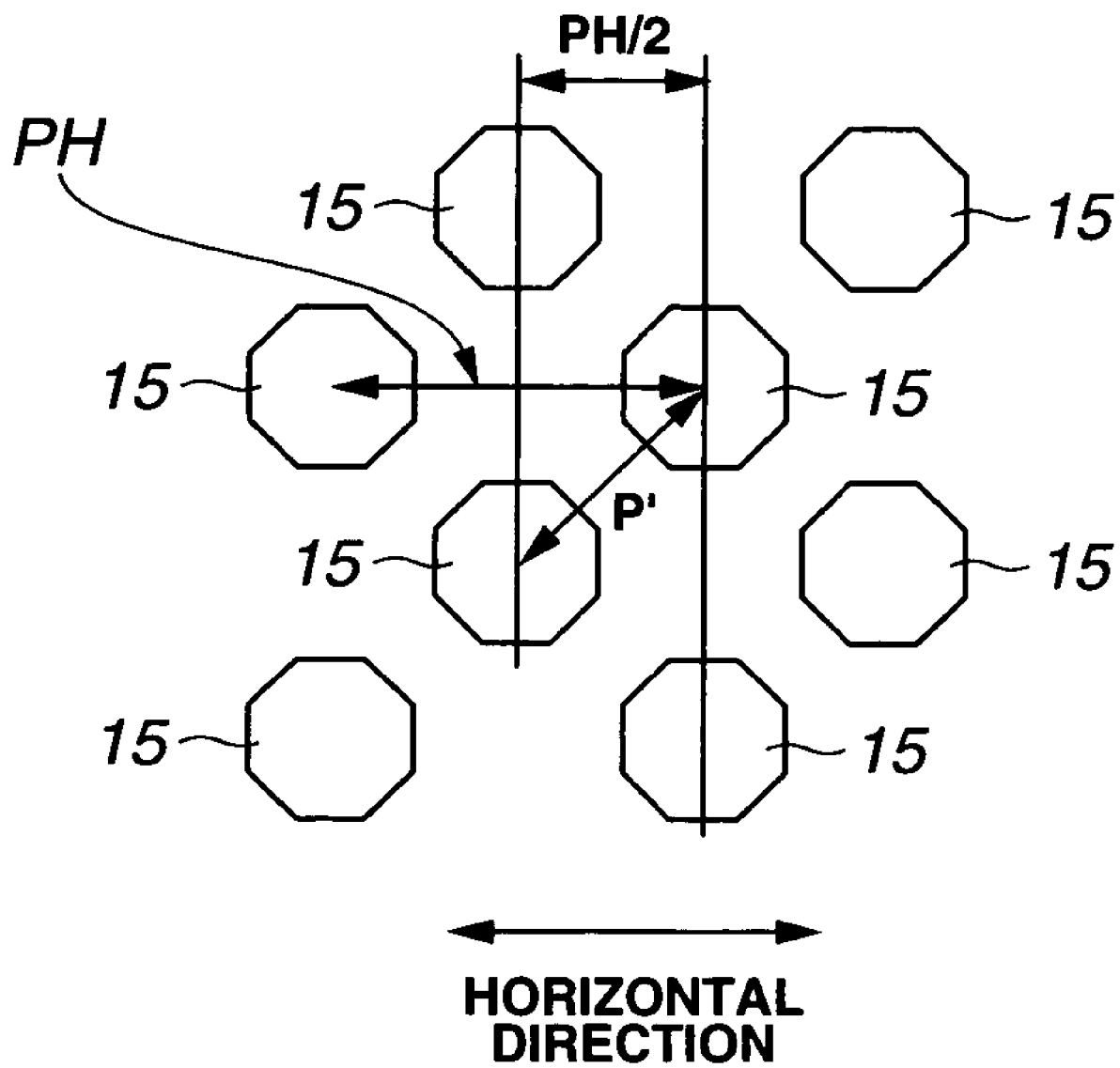
FIG. 18 is an explanatory diagram of a solid state image pickup device in which an array of pixels is arranged with being shifted by ½ of a horizontal pitch every horizontal line.

Furthermore, recently, as shown in FIG. 18, there have been solid state image pickup devices having such structure that positions of pixels have been arranged with being shifted by PH/2 to a horizontal pixel pitch PH every one horizontal line of a pixel array. It is reported that, in the case of such a solid state image pickup device, a generation method of a luminance signal is different from a conventional solid state image pickup device in which pixels are arrayed horizontally and vertically in a grid pattern, and a resolution in an image signal outputted is equivalent to that of a conventional solid state image pickup device with 1.6 times of pixel count in which pixels are arrayed horizontally and vertically in a grid pattern. (Society of Photographic Science and Technology of Japan, 63(3), 1-5 (2000))

Hence, let a pixel pitch in an oblique direction be P' in FIG. 18, and it is applicable to the endoscope and endoscope apparatus of the present invention by converting it into a horizontal pixel pitch P with the following expression.

$$P = P \times \sqrt{1.6}$$

Next, a so-called three-sensor image pickup unit using a system of generating one image signal using three solid state image pickup devices will be discussed.

In the three-sensor system, light from an object is divided into three by a prism, which are assigned to solid state image pickup devices corresponding to respective three primary colors of R, G, and B. In each solid state image pickup device, a color luminance signal corresponding to each pixel is generated. Then, one luminance signal and one color information are obtained from three of an R luminance signal, a G luminance signal, and a B luminance signal. At this time, values of IH/P, Fl/P, and Fno. become the same values in all the three solid state image pickup devices.

Hence, in the case of three-sensor system, by regarding it similarly to the case of a solid state image pickup device which generates a luminance signal every pixel, it is applicable to the endoscope and endoscope apparatus of the present invention.

What is claimed is:

1. An endoscope which is equipped with a fixed focus image pickup unit which is constructed of an objective optical system, and a solid state color image pickup device in which a color filter is arranged every pixel, comprising:
    the solid state image pickup device that fulfills a conditional expression (1); and
    the objective optical system that fulfills a conditional expression (2) and a conditional expression (3),
    wherein an image pickup plane of the solid state image pickup device is arranged in a position where an MTF on an optical axis in a spatial frequency 1/(3×P) of the objective optical system at 4 mm of object distance, and an MTF on the optical axis in the spatial frequency 1/(3×P) at 50 mm of object distance become 10% or more together:

$$300 < IH/P < 550 \quad \text{conditional expression (1)}$$

$$300 < Fl/P < 550 \quad \text{conditional expression (2)}$$

$$2400 \times P < Fno. < 4200 \times P \quad \text{conditional expression (3)}$$

where
    P: horizontal pixel pitch [mm] of solid state image pickup device
    IH: distance [mm] to most distant position from center in display area of solid state image pickup device
    Fl: focal length [mm] of objective optical system
    Fno.: effective f-number of objective optical system.

2. The endoscope which is equipped with a fixed focus image pickup unit, according to claim 1, wherein an endoscope insertion section is further equipped with a treatment tool insertion channel, and the image pickup unit and the treatment tool insertion channel are arranged so that at least a part of a treatment tool may enter within a visual field of the image pickup unit when the treatment tool is protruded through the channel for treatment from an end of the endoscope insertion section by 4 mm of distance.

3. An endoscope apparatus which is equipped with an endoscope which includes at least a fixed focus image pickup unit, and a display means which displays an image which the image pickup unit acquires, comprising:
    the image pickup unit that is constructed of a solid state image pickup device in which a color filter is arranged every pixel, and which fulfills a conditional expression (1), and an objective optical system which fulfills a conditional expression (2) and a conditional expression (3),
    wherein, with letting a range of the image pickup unit in an object side, where a resolution in a center of an image displayed on the display means is 25 lines/mm or more, be d1, and letting a range of the image pickup unit in the object side, where a resolution in a center of an image displayed on the display means is 2 lines/mm or more, be d2, an image pickup plane of the solid state image pickup device is arranged near an image forming position of the objective optical system so that an object point on an optical axis which is at a position apart by 3.5 mm from a plane of the objective optical system in a side nearest to the object which constructs an image pickup unit may be included in both of d1 and d2, and so that an object point on the optical axis which is at a position apart by 50 mm from the plane of the objective optical system in the side nearest to the object which constructs the image pickup unit may be included in only d2:

$$300 < IH/P < 550 \quad \text{conditional expression (1)}$$

$$300 < Fl/P < 550 \quad \text{conditional expression (2)}$$

$$2400 \times P < Fno. < 4200 \times P \quad \text{conditional expression (3)}$$

where
    P: horizontal pixel pitch [mm] of solid state image pickup device
    IH: distance [mm] to most distant position from center in display area of solid state image pickup device
    Fl: focal length [mm] of objective optical system
    Fno.: effective f-number of objective optical system.

4. The endoscope apparatus according to claim 3, wherein an endoscope insertion section is further equipped with a treatment tool insertion channel, and the image pickup unit and the treatment tool insertion channel are arranged so that at least a part of a treatment tool may enter within a visual field of the image pickup unit when the treatment tool is protruded through the channel for treatment from an end of the endoscope insertion section by 4 mm of distance.

5. An endoscope apparatus which is equipped with a fixed focus image pickup unit which forms an objective image with an objective optical system, and which acquires an image signal with a solid state image pickup device in which a color filter is arranged every pixel near an image-forming plane of the objective optical system, and a circuit system which processes the image signal sent from the solid state image pickup device, comprising:

the solid state image pickup device that fulfills a conditional expression (1); and the objective optical system that fulfills a conditional expression (2) and a conditional expression (3), wherein it has a resolution of 35 μm or more when a distance from the objective optical system to an object is 4 mm, and has a resolution of 0.45 mm or more when the distance from the objective optical system to the object is 50 mm:

$300 < IH/P < 550$    conditional expression (1)

$300 < Fl/P < 550$    conditional expression (2)

$2400 \times P < Fno. < 4200 \times P$    conditional expression (3)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system.

6. The endoscope apparatus according to claim 5, wherein an endoscope insertion section is further equipped with a treatment tool insertion channel, and the image pickup unit and the treatment tool insertion channel are arranged so that at least a part of a treatment tool may enter within a visual field of the image pickup unit when the treatment tool is protruded through the channel for treatment from an end of the endoscope insertion section by 4 mm of distance.

7. An endoscope which is equipped with a fixed focus image pickup unit which is constructed of an objective optical system, and a solid state image pickup device in which a luminance signal is generated every pixel, comprising:

the solid state image pickup device that fulfills a conditional expression (4); and the objective optical system that fulfills a conditional expression (5) and a conditional expression (6), wherein an image pickup plane of the solid state image pickup device is arranged in a position where an MTF on an optical axis in a spatial frequency 1/(2×P) of the objective optical system at 4 mm of object distance, and an MTF on the optical axis in the spatial frequency 1/(2×P) at 50 mm of object distance become 10% or more together:

$200 < IH/P < 360$    conditional expression (4)

$200 < Fl/P < 360$    conditional expression (5)

$1600 \times P < Fno. < 2800 \times P$    conditional expression (6)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system.

8. The endoscope apparatus which is equipped with a fixed focus image pickup unit, according to claim 7, wherein an endoscope insertion section is further equipped with a treatment tool insertion channel, and the image pickup unit and the treatment tool insertion channel are arranged so that at least a part of a treatment tool may enter within a visual field of the image pickup unit when the treatment tool is protruded through the channel for treatment from an end of the endoscope insertion section by 4 mm of distance.

9. An endoscope apparatus which is equipped with an endoscope which includes at least a fixed focus image pickup unit, and a display means which displays an image which the image pickup unit acquires, comprising:

the image pickup unit that is constructed of a solid state image pickup device in which a luminance signal is generated every pixel, and which fulfills a conditional expression (4), and an objective optical system which fulfills a conditional expression (5) and a conditional expression (6), wherein, with letting a range of the image pickup unit in an object side, where a resolution in a center of an image displayed on the display means is 25 lines/mm or more, be d1, and letting a range of the image pickup unit in the object side, where a resolution in a center of an image displayed on the display means is 2 lines/mm or more, be d2, an image pickup plane of the solid state image pickup device is arranged near an image forming position of the objective optical system so that an object point on an optical axis which is at a position apart by 3.5 mm from a plane of the objective optical system in a side nearest to the object which constructs an image pickup unit may be included in both of d1 and d2, and so that an object point on the optical axis which is at a position apart by 50 mm from the plane of the objective optical system in the side nearest to the object which constructs the image pickup unit may be included in only d2:

$200 < IH/P < 360$    conditional expression (4)

$200 < Fl/P < 360$    conditional expression (5)

$1600 \times P < Fno. < 2800 \times P$    conditional expression (6)

where
P: horizontal pixel pitch [mm] of solid state image pickup device
IH: distance [mm] to most distant position from center in display area of solid state image pickup device
Fl: focal length [mm] of objective optical system
Fno.: effective f-number of objective optical system.

10. The endoscope apparatus according to claim 9, wherein an endoscope insertion section is further equipped with a treatment tool insertion channel, and the image pickup unit and the treatment tool insertion channel are arranged so that at least a part of a treatment tool may enter within a visual field of the image pickup unit when the treatment tool is protruded through the channel for treatment from an end of the endoscope insertion section by 4 mm of distance.

11. An endoscope apparatus which is equipped with a fixed focus image pickup unit which forms an objective image with an objective optical system, and which acquires an image signal with a solid state image pickup device in which a luminance signal is generated every pixel near an image-forming plane of the objective optical system, and a circuit system which processes the image signal sent from the solid state image pickup device, comprising:

the solid state image pickup device fulfills a conditional expression (4), the objective optical system that fulfills a conditional expression (5) and a conditional expression (6), wherein the endoscope apparatus has a resolution of 35 μm or more when a distance from the objective optical system to an object is 4 mm, and has a resolution of 0.45 mm or more when the distance from the objective optical system to the object is 50 mm:

$$200 < IH/P < 360 \qquad \text{conditional expression (4)}$$

$$200 < Fl/P < 360 \qquad \text{conditional expression (5)}$$

$$1600 \times P < Fno. < 2800 \times P \qquad \text{conditional expression (6)}$$

where
- P: horizontal pixel pitch [mm] of solid state image pickup device
- IH: distance [mm] to most distant position from center in display area of solid state image pickup device
- Fl: focal length [mm] of objective optical system
- Fno.: effective f-number of objective optical system.

12. The endoscope apparatus according to claim 11, wherein an endoscope insertion section is further equipped with a treatment tool insertion channel, and the image pickup unit and the treatment tool insertion channel are arranged so that at least a part of a treatment tool may enter within a visual field of the image pickup unit when the treatment tool is protruded through the channel for treatment from an end of the endoscope insertion section by 4 mm of distance.

* * * * *